(12) United States Patent
Van Gompel et al.

(10) Patent No.: US 7,621,900 B2
(45) Date of Patent: Nov. 24, 2009

(54) DISPOSABLE ABSORBENT GARMENT THAT INCORPORATES A CONTINUOUS REINFORCED LEG GASKET AND METHOD FOR THE MANUFACTURE THEREOF

(75) Inventors: Paul T. Van Gompel, Hortonville, WI (US); Russell E. Thorson, Appleton, WI (US); Cynthia D. Maas, Appleton, WI (US); Kenneth J. Wagner, Greenville, WI (US); Thomas J. Vanselow, Appleton, WI (US)

(73) Assignee: Kimberly-Clark Worldwide, Inc., Nennah, WI (US)

( * ) Notice: Subject to any disclaimer, the term of this patent is extended or adjusted under 35 U.S.C. 154(b) by 1075 days.

(21) Appl. No.: 10/746,212

(22) Filed: Dec. 23, 2003

(65) Prior Publication Data

US 2005/0137563 A1 Jun. 23, 2005

(51) Int. Cl.
*A61F 13/15* (2006.01)
*A61F 13/20* (2006.01)

(52) U.S. Cl. .............................. 604/385.24; 604/385.01

(58) Field of Classification Search ................. 604/367, 604/385.01, 385.04, 385.08, 385.24–385.25, 604/385.27–385.28

See application file for complete search history.

(56) References Cited

U.S. PATENT DOCUMENTS

| 4,900,384 | A | 2/1990 | Sanders et al. |
| 6,168,585 | B1 * | 1/2001 | Cesco-Cancian ....... 604/385.26 |
| 6,340,782 | B1 | 1/2002 | Kling et al. |
| 6,440,239 | B1 | 8/2002 | Vogt |
| 2003/0135189 | A1 | 7/2003 | Umebayashi |

FOREIGN PATENT DOCUMENTS

EP 0951890 * 10/1999

* cited by examiner

*Primary Examiner*—Michele Kidwell
(74) *Attorney, Agent, or Firm*—Thomas Connelly; Sebastian C. Pugliese; Bryan R. Rosiejka

(57) ABSTRACT

A method of manufacturing a disposable absorbent article incorporating a reinforcement element adjacent a crotch edge of a body panel includes moving a web of body panel material in a longitudinal machine direction, applying a plurality of reinforcement elements to an outer surface of the web and cutting the web of body panel material along the longitudinal machine direction to thereby form a rear body panel web and a front body panel web each having a terminal crotch edge and at least a portion of the reinforcement elements secured thereto. The method further includes connecting a crotch member to each of the rear and front body pane webs thereby bridging the gab between. A disposable absorbent article incorporating a reinforcement element is also provided.

26 Claims, 7 Drawing Sheets

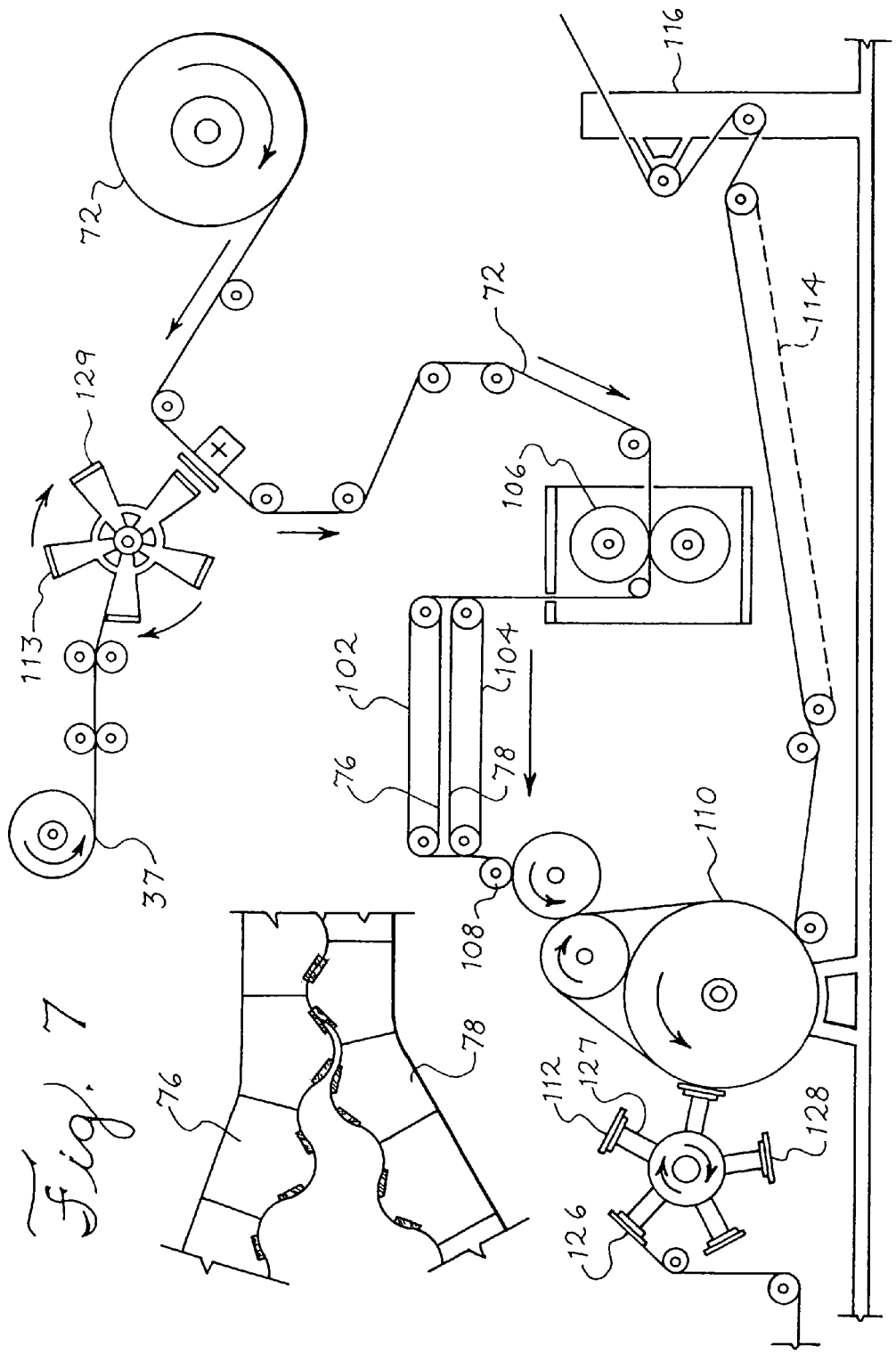

DISPOSABLE ABSORBENT GARMENT THAT INCORPORATES A CONTINUOUS REINFORCED LEG GASKET AND METHOD FOR THE MANUFACTURE THEREOF

BACKGROUND

The present invention relates generally to disposable undergarments, and in particular, to a three-piece undergarment having reinforcement elements at specific locations corresponding to the leg openings of the article and the method for the manufacture thereof from a nested front and rear body panel web.

Disposable undergarments can be configured in many different forms. For example, disposable absorbent garments can be configured as a pant-type, pull-on garment, or as a diaper-type product that is drawn up between the legs and fastened about the waist with various fastening systems. Often, absorbent garments include an outer cover, which forms at least a part of a body panel that is secured around the waist of the user. In addition, the outer cover typically extends along a crotch region of the garment.

Often, the outer cover is made from a single piece of material, with leg openings cut therein, for example by die cutting. The material from the leg cut out, which can account for as much as 20-30% of the total area of the outer cover, typically is waste material, which must be disposed of or recycled.

In response to this problem of waste, some garments are configured with front, rear and crotch sections formed from a single web that is divided into two nested halves, as disclosed for example in U.S. Pat. No. 5,858,151. However, the webs of the U.S. Pat. No. 5,858,151 have overlapping crotch portions that are directly secured one to the other. Accordingly, the overall rise of the garment is not readily varied to accommodate different size users, and the range of sizes is limited by the extent of the overlapping regions.

Moreover, the size of the leg openings formed by a die cutter in a conventional one-piece outer cover is typically fixed. As such, it can be expensive and time consuming, and reduces the overall flexibility of the manufacturing line, to switch dies and alter the process to manufacture different size garments.

Often elastic elements are secured between two or more layers of the body panel material in a pattern that attempts to match the crotch edge of the body panels. However, the shape of the elastic elements may not be congruent with the curve of the leg opening and may vary not only in the placement but also in the ability to securely fit around the circumference of the user's leg. Consequently, after continued and prolong use, the leg openings lose their elasticity around the user's leg allowing leakage of bodily exudates. In addition, there is a risk of inadvertently cutting the elastic elements when forming the crotch edge.

Therefore, the need remains for improved methods and assemblies for manufacturing undergarments to reduce the waste of materials while providing undergarments with elastic elements that fit the curve of the leg opening to provide additional reinforcement during use.

SUMMARY

Briefly stated, in one embodiment described below, a method of manufacturing an undergarment includes moving a web of body panel material in a longitudinal machine direction. The method further includes applying a plurality of reinforcement elements to the outer surface of the web of body panel material. The method also includes cutting the web of body panel material along a longitudinal machine direction and thereby forming a front body panel web and a rear body panel web, with at least one of the front and rear body panels having at least a portion of a reinforcement element applied thereto. In addition, the method includes connecting a crotch member to each of the front and rear body panel webs.

In one aspect, the method includes shifting at least one of the rear and front body panel webs in the longitudinal machine direction as well as separating the rear and front body panel webs in a lateral cross direction. In one embodiment, cutting of the web of body panel material along the longitudinal machine direction includes cutting at least some of the reinforcement elements and thereby providing at least a portion of the reinforcement elements on each of the front and rear body panels. In another embodiment, the front and rear body panel webs are cut along the lateral cross direction. Also in one embodiment, the crotch member is folded.

In another aspect, one embodiment further includes applying a plurality of reinforcement elements to the outer surface of the web of body panel material wherein at least some of the reinforcement elements are not parallel to the longitudinal machine direction.

In another aspect, one embodiment of the method further includes applying at least one reinforcement element at specific locations that correspond to the open leg regions that do not overlap the absorbent insert. In various embodiments, the reinforcement elements are positioned along one or more of the outer lateral edges of the inner cut edge of one or more of the webs.

In yet another aspect, a disposable undergarment includes a front and rear body panel each having a pair of opposite side edges, a terminal waist edge, a terminal crotch edge and at least one reinforcement element secured along one of said terminal crotch edges. A crotch member is connected to the front and rear body panels.

The various embodiments provide significant advantages over other absorbent garments and methods of manufacture. In particular, the reinforcement elements can be easily and simply located on the web of body panel material without having to precisely match the contour of the cut crotch edge. Instead, the reinforcement elements, which have a width, provide some tolerance for the cutting operation. In addition, the reinforcement elements provide additional strength and elasticity along the leg openings of the garment.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 7 is a schematic illustration of a system for manufacturing a disposable garment.

DETAILED DESCRIPTION OF THE PRESENTLY PREFERRED EMBODIMENTS

It should be understood that the term "longitudinal," 500 as used herein, means of or relating to length or the lengthwise direction. The term "laterally," 502 as used herein means situated on, directed toward or running from side to side.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by the user, and regardless of whether any such outer garments are actually worn regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, a first component such as a web may be traveling a first machine direction, which is substantially perpendicular to the travel of another component, such as an absorbent insert, in a second machine direction. The term "cross direction" means the direction substantially perpendicular to the machine direction.

The term "web" refers to a continuous stream of material, whether made from one or more layers or substrates, and regardless of whether it may have non-continuous, discrete items disposed thereon.

The terms "connecting," "coupled," "attached," and "secured," and variations thereof, broadly covers two or more items being directly connected one to the other, or by way of one or more intervening members or components.

The term "disposable" as used herein means a product that is intended for a single use, and/or a product that is used until soiled.

Figure 4:
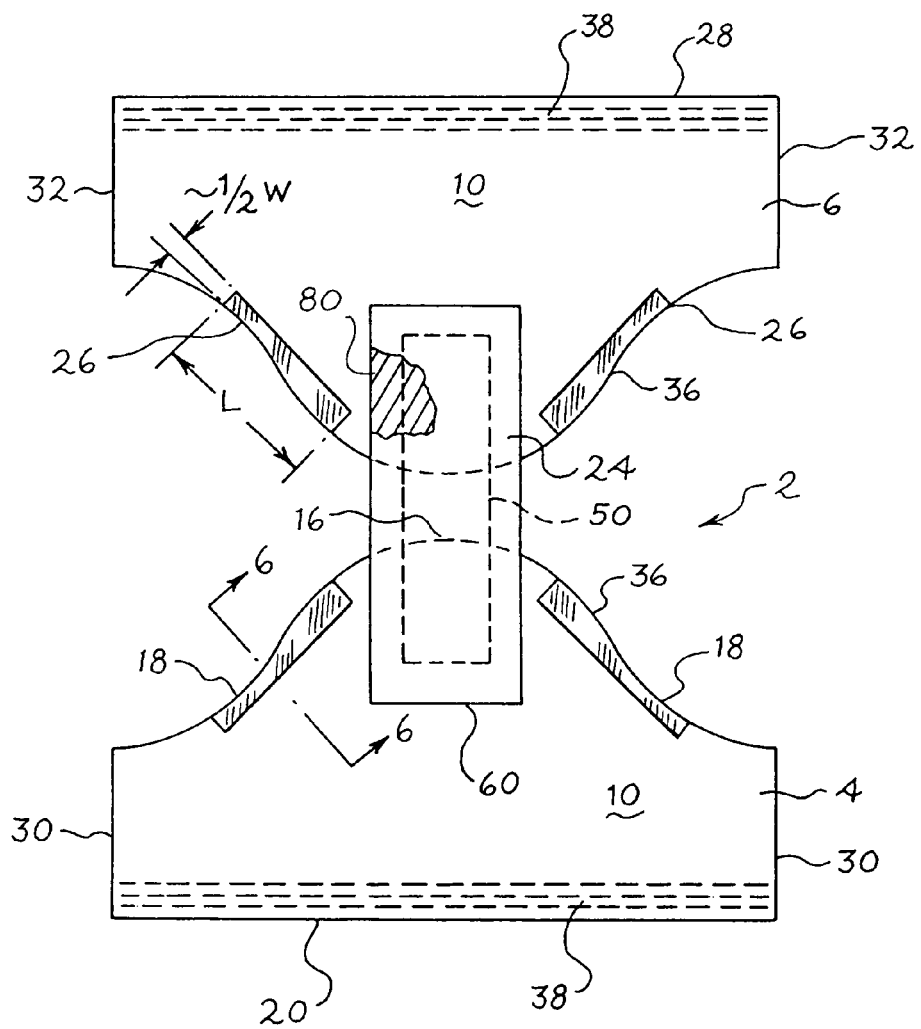
FIG. 4 is a plan view of a disposable garment in an unfolded configuration having a front and rear body panel formed from the front and rear body panel webs shown in FIG. 3.
Figure 5:
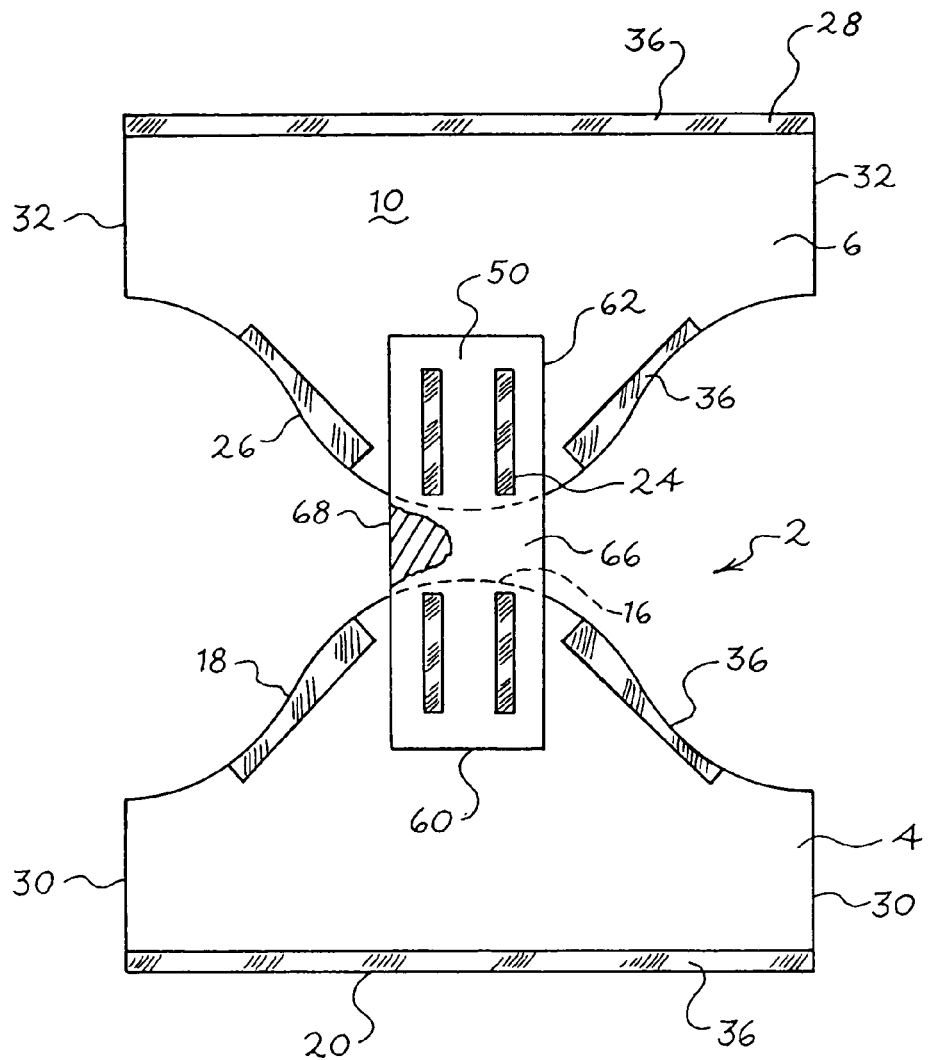
FIG. 5 is alternative embodiment of disposable garment in an unfolded configuration.
Figure 6:
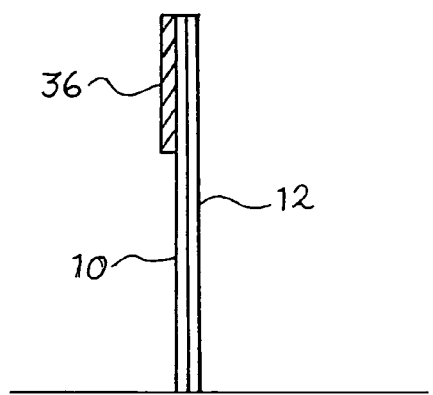
FIG. 6 is a cross section illustration of the reinforcement element taken along line 6-6 of FIG. 4.

Referring to FIGS. 4-6, an undergarment 2 includes a first, front body panel 4 and a second, rear body panel 6. The term "body panel" refers to the portion(s) of the undergarment, whether made of one or more layers or substrates or of one or more pieces or components that is/are fitted circumferentially around at least the waist region of the user, including for example the user's lower back, buttock, hips and abdomen. The first and second body panels each have an inner, body side surface 10 and an outer, garment side surface 12. The first, front body panel 4 has a first crotch edge forming a crotch portion 16 and leg opening portion 18 and a first terminal edge 20 which is preferably linear but can assume other shapes. Likewise, the second, rear body panel 6 has a second crotch edge forming a crotch portion 24 and a leg opening portion 26 and a second terminal edge 28, which is preferably linear but can assume other shapes. Each of the first and second body panels has an outboard side edge 30, 32 formed along the outer periphery of the opposite side portions of the first and second body panel. It should be understood that the outboard side edges of the front and rear body panels can have different lengths relative to each other.

Referring to FIGS. 4 and 5, one or more, and preferably a plurality, meaning two or more, reinforcement elements 36 are secured to each of the first and second body panels along the leg opening portions 18, 26 of the crotch edges. In one embodiment, the reinforcement elements 36 have a length (L) of between about 4 and 12 inches either extended or applied non-extended to those lengths. and a width (½ W) of between about 0.25 and 1 inches. It should be understood that the length and width of the individual reinforcement element can vary based upon the desired configuration of the absorbent garment.

In one embodiment, shown in FIG. 5, a reinforcement element 36 extends across substantially the entire waist portion of the front and rear body panel 4, 6, and a plurality of reinforcement elements are secured along the leg openings 18, 26. In various alternative embodiments, the reinforcement elements can extend along the entirety of the crotch edge, and along only a portion of the waist edge. The reinforcement elements 36 increase the force to elongate the corresponding region of the leg openings 18, 26 and waist edge 20, 28.

As shown in FIGS. 2-5, the reinforcement elements 36 overlap the longitudinal cut, the location of the die cut after the reinforcement element has been applied, defining the front and back body panels and allows the die cutter or slitter to cut the reinforcement element 36 to match the curved shape of the leg openings 18, 26. The reinforcement element 36 can be fixedly secured to the garment side or the body side of the front and rear body panels. As shown in FIGS. 4 and 5, the reinforcement elements 36 are attached to the outermost body side surface 10 of the front and rear body panels 4, 6. In this embodiment, the reinforcement elements are secured along the crotch edge 16, 24. In addition, the reinforcement element 36 can be secured to the either of the front and rear body panels only, for example when they are positioned on either side of the longitudinal cut, or can be secured to both the front and rear body panels.

The reinforcement element strengthens the body panels in the leg opening 18, 26 regions of the garment. It should be understood, that the reinforcement elements can be made as a continuous strip or discrete elements spaced along the crotch edge defining the leg openings 18, 26. The reinforcement element can also be applied to the terminal waist edge of both or either of the front and rear body panels 4, 6. The various reinforcement elements 36 can be formed from rubber or other elastomeric materials.

Referring to FIG. 6, in one embodiment, the reinforcement elements 36 are made from various types of elastic films, laminates or composites of material that provide stretchability with the ability to return to its normal shape and/or length. In various embodiments, the reinforcement element 36 is made of a Stretch bonded laminate (SBL) or a Necked Bonded Laminate (NBL) or other types of elastic laminates that provide stretchability with retraction while providing a cloth-like texture and breathability. In one embodiment, the reinforcement element 36 is made of a single layer of an elastic film or non-woven material that can be attached to the front and rear body panels 4, 6 for example by bonding, including adhesive, thermal and/or ultrasonic bonding. In one embodiment, the reinforcement element 36 includes elastic strands of Lycra® elastic material that are attached, for example and without limitation with adhesive, laminated between two non-woven facings, such as 0.5 osy polypropylene spunbond or a low basis weight bonded carded web. Other means of reinforcing the body panels in the leg opening 18, 26 and the terminal waist edge of both or either of the front and rear body panels 4, 6 can be accomplished by applying a coating of polyethylene adhesive, silicon, latex or any other type of coatings that reinforce those specific regions. The reinforcement element 36 could further include spray adhesive, silicone or latex coatings. The reinforcement element 36 can be elongated or non-elongated when applied to the web 72 of body panel material. Similarly, the web 72 of body panel material can be elongated or non-elongated when the reinforcement elements 36 is applied thereto.

The material dimensions of each individual reinforcement element 36 can range in length (L) from about 10 to 50% of the total lateral width of the final garment product, for example, the lateral width of the front and/or rear body panels measured from side to side. In one embodiment, the length of each reinforcement element 36 is about 20% to 45% of the total lateral width of the garment. In another embodiment, the length of the reinforcement element 36 is from about 25% to 40% of the total lateral width of the garment. It should be understood that the material properties and material dimensions (i.e. the length and the width) can be varied depending on the desired use of the web 72 of body material. It should also be understood that additional elastic elements may be incorporated into the body panel, for example by disposing the elastic elements between two layers of non-women material along the crotch edge so as to form leg elastics.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in an alternative embodiment, one or more separate waist bands or reinforcement elements 36, with or without elastic elements, can be secured to one or both of the rear and front body panels, preferably along the upper terminal edges 20, 28 thereof.

Referring to FIGS. 1A-5, each body panel 4, 6 is preferably formed as a composite, or laminate material, otherwise referred to as substrates or laminates, with the plurality of elastic strands sandwiched therebetween. Preferably two or more layers are bonded with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along the lateral article width. Examples of such elastomeric composite materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability.

The body panels can be composed of materials that are elastic or elastomeric and exhibit biaxial stretch characteristics or MD/CD stretch characteristics, or that are extensible composites. The terms elastic, elastomeric, elastomer, or stretchable can be used interchangeable that defines a material that can be elongated, stretched or extended (deformed) beyond its initial form or state and will tend to retract (resume to its initial form or state) after it has been deformed. Additional waist and leg elastic elements can be added from the leg openings, but are not necessarily required by, the body panels.

In one embodiment, the entirety of the body panels are elasticized, such that the entire body panel conforms to the body of the user without any spacing between the body panel and the user's body, and without the attendant bulkiness of a non-elasticized material. The body panels are breathable, cloth-like, multi-directional non-woven laminates with stretch and/or extensible properties. In one embodiment, the non-woven layers are pre-necked, preferably between about 10% and about 80%, in the longitudinal direction, which provides extensibility in the longitudinal direction with minimum force.

The terms "extensible," "extensibility," and variations thereof as used herein means capable of being extended, and providing a selected elongation, for example between about 5% and about 70%, when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occurs at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the preferred non-woven material provides an increase in surface area without the retractive force of elastomeric materials. In one embodiment, body panel is extensible in at least the cross-direction, or longitudinal direction, with the material providing an elongation of at least about 1 cm when subjected to a tensile force of 11.8 grams per cm. In addition, the body panel preferably provides a substantially permanent deformation of at least about 20% when it is subjected to a tensile force of 19.70 grams per cm and is then allowed to relax under a zero applied stress for a period of one minute. Of course, it should be understood that the body panel can also be made extensible in the lateral direction.

In one embodiment, the front and rear body panels 4, 6 are made of non-woven laminates of two layers of longitudinally extensible 0.60 osy polypropylene spunbond material with elongated strands of Lycra® elastics sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral cross direction thereby creating an elastically gathered non-woven body panel with longitudinal extensibility. The term "gather," and variations thereof, as used herein means puckered, or contracted into folds or wrinkles, which should be understood as including micropleats. In this way, the body panels 4, 6 can be elongated in both the longitudinal and lateral direction to conform to the body of the user when the garment is applied thereto. In particular, as the user pulls the garment up over their hips, the non-woven laminate body panels stretch in the lateral direction while the reinforcement elements forming the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements 38, incorporated in one embodiment as shown in FIG. 4, will increase.

The body panel 4, 6 non-woven material is preferably substantially hydrophobic, which may optionally be treated with a surfactant or otherwise processed to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIGS. 4 and 5, a crotch member 50 connecting the front and rear body panels 4, 6 can be folded such that the side edges 30, 32 of the front and rear body panels 4, 6 are aligned wherein they can be fixedly secured at a seam. The seam can be formed by bonding, sewing or otherwise attaching the side edges. Alternatively, the product can remain "open," wherein the body panels are releasably secured with one or more fastening members as explained below.

In one embodiment (not shown), the garment includes a combination of side edges that are secured to form a seam and fastening members that allow the fit of the undergarment to be adjusted. For example, fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. Preferably, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members preferably include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to FIGS. 4 and 5, in one embodiment the undergarment is disposable and is also configured as an absorbent undergarment. In the absorbent garment, the crotch member includes an absorbent insert 50 having first and second opposed terminal end edges 60, 62. In one preferred embodiment, the absorbent insert preferably includes a substantially liquid permeable topsheet 66, or liner, and a substantially liquid impermeable backsheet 68, or outer cover. A retention portion 80 is disposed or sandwiched between the topsheet 66 and the backsheet 68, which are connected. The topsheet 66, backsheet 68 and other components of the absorbent insert 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet 66 and backsheet 68, or any of the other components described herein. It should be understood that the term "absorbent insert" refers to any material or assembly capable of absorbing liquids or bodily exudates, and may be comprised of a single material or component, for example a retention portion, or can be formed as a composite of several components. It should also be understood that the term "crotch member" refers to any member made of any material, including for example and without limitation those described herein with respect to the body panels and absorbent inserts, and is not limited to absorbent inserts and/or materials. The crotch member may be made of one or more layers of a non-woven material.

In one embodiment, additional layers, including for example, a surge layer, are also preferably incorporated into the absorbent insert. Preferably, the surge layer does not run the entire length of the absorbent insert and is shorter than the retention portion. The topsheet 66 can be indirectly joined to the backsheet 68 by affixing the topsheet 66 to intermediate layers, such as the surge layer or retention portion, which in turn is affixed to the backsheet 68. The absorbent insert 50 also may include barrier cuffs, or leakage control shields, formed along the opposite longitudinally extending edges of the absorbent composite.

The backsheet 68 is preferably liquid impermeable, but may be liquid permeable, e.g., when an additional barrier layer is used with the retention portion. For example, in one embodiment, the backsheet 68 can be made from a thin plastic film, or other flexible, substantially liquid-impermeable material. As used herein, the term "flexible" means a material that is compliant and which will readily conform to the general shape and contour of the body of the user. The backsheet 68 prevents various bodily fluids and exudates from wetting or otherwise contaminating various bedding or outer garments worn by the user over the absorbent garment. In particular, the backsheet 68 can include a film, such as a polyethylene film, having a thickness of from about 0.012 mm to about 0.051 mm.

In various constructions, the topsheet 66 can comprise various woven or nonwoven materials. For example, the topsheet 66 can be composed of a meltblown or spunbonded web of desired fibers, and may also be a bonded-carded web. In another example, the topsheet 66 can be made of a substantially hydrophobic material, and the hydrophobic material may optionally be treated with a surfactant or otherwise processed to import a desired level of wettability and hydrophilicity. In one particular embodiment of the invention, the topsheet 66 is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet 68 can comprise a woven or nonwoven fibrous web layer, which is treated or constructed, partially or wholly, to impart the desired levels of liquid impermeability to selected regions that are adjacent to or proximate the absorbent retention portion 80. For example, the backsheet 68 may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet 68 can provide the outercover of the article, particularly in the crotch region. Optionally, however, the article may include a separate outercover component member, as disclosed herein, which is additional to the backsheet 68. The outercover can be joined, for example, to one or more of the absorbent composite and/or body panels as explained above.

The backsheet 68 may include a micro-porous, "breathable" material which permits gases, such as water vapor, to escape from the absorbent garment while substantially preventing liquid exudates from passing through the backsheet 68. For example, the breathable backsheet 68 may be composed of a microporous polymer film or a non-woven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet 68 may also be embossed or otherwise provided with a pattern or matte finish to exhibit a more aesthetically pleasing appearance.

In various configurations of the invention, where a component, such as the backsheet 68 is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet 68 is sufficiently impermeable to liquid and semi-liquid materials to substantially prevent the undesired leakage of waste materials, defined as exudates, including for example urine and feces. For example, the backsheet 68 can desirably support a hydrohead of at least about 45 centimeters (cm) substantially without leakage. The backsheet 68 can alternatively support a hydrohead of at least about 55 cm, and optionally, can support a hydrohead of at least about 60 cm, or more, to provide improved benefits.

The backsheet 68 and/or outercover also can be extensible. In one embodiment, the backsheet 68 and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet 68 and/or outercover also can be expandable, for example when it has one or more folds, e.g., one or more z-folds (not shown), or can be both extensible and expandable. The term expandable as used herein means to enlarge or to increase the extent or area, lateral and/or longitudinal by unfolding one or more folds.

The retention portion 80 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 80 preferably can be made of a single or dual layer of absorbent material. The retention portion 80 preferably has an hour-glass shape with enlarged end regions. Alternatively, the retention portion 80 can include a folded or multi-layered configuration. The retention portion 80 preferably has a length substantially equal to, or slightly shorter than, the length of the absorbent insert. The retention portion 80 can include one or more barrier layers attached to the absorbent material. In one embodiment, an upper tissue substrate is disposed adjacent the retention portion. Alternatively, a lower tissue substrate can be disposed adjacent an opposite side of the retention portion 80, or the tissue can completely envelope the retention position 80.

Figure 3:
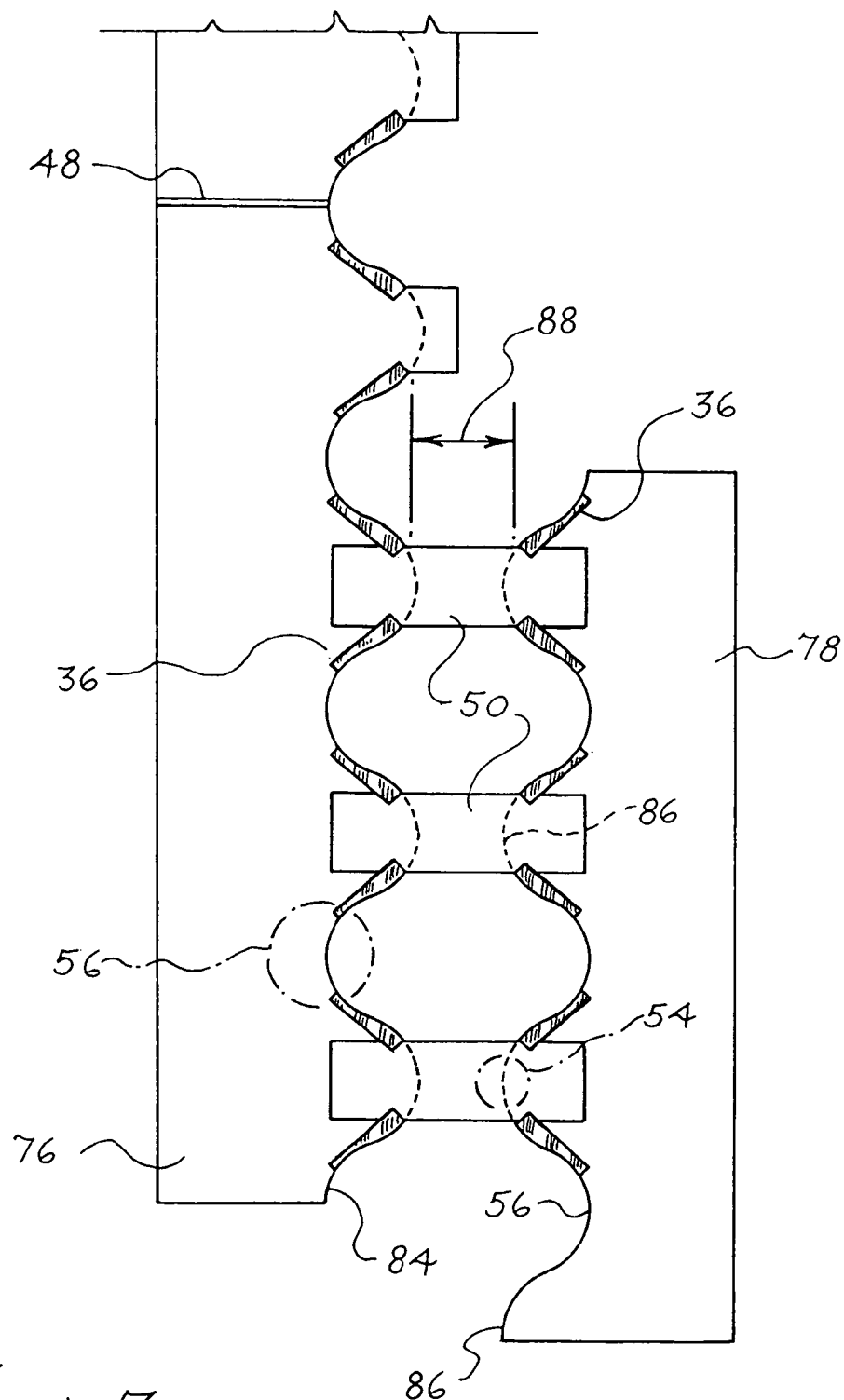
FIG. 3 is a plan view of a web of body panel material separated in the cross direction and aligned in the machine direction.

Referring to FIGS. 3-5, the opposite garment side of the end regions of the crotch member 50, and in particular, the outer, garment side surface of the backsheet 68, are secured to the bodyside surface of the opposed crotch portions 16, 24 of the first and second body panels 4, 6. It should be understood that in one embodiment, the crotch member, for example the body side thereof, can be secured to the garment side surface of the first and second body panels. It should be understood that the crotch member 50 can be secured using any of the methods of attachment described above, including for example various adhesives, stitching or other bonding methods. The crotch member can be secured to the body panels with any configuration of attachment lines, swirls, patterns, spots, etc., or can be a full and continuous attachment therebetween.

The entire portion of the crotch member 50 overlapping the body panels 4, 6 can be attached thereto, or the crotch member can be minimally attached to the body panels, for example by one or more lines of attachment formed along the centerline of the absorbent composite, or along a line adjacent the crotch portions 16, 24 of the body panels, so as to allow the body panels to stretch from side to side and extend from front to back, or from the crotch to the waist.

Referring to FIG. 7, the method for fabricating one or more embodiments of the aforedescribed garments is illustrated. In one embodiment, the method of fabrication includes moving a web 72 of body panel material in a longitudinal machine direction 500 and cutting the web in the longitudinal machine direction 500 to form a front and rear body panel web 76, 78 having at least one reinforcement element securably attached to the body side or garment side of the body panel web 2.

Each body panel web includes an outer lateral edge 80, 82 and an inner cut edge 84, 86. In one embodiment, shown for example in FIG. 3, the inner cut edges 84, 86 of the front and rear body panel webs correspond, or mate such that they have the same shape. In such an embodiment, no waste material is generated.

In an alternative embodiment, (not shown), the wave pattern defining the first and second cut edges 84, 86 has a first and second shape formed on opposite sides of a wave baseline which extend in the longitudinal machine direction approximately half way between the peaks 54 and valleys 56 of the cut edges. In this embodiment, the first shape is different from the second shape, with each shape having a different curvature. In this way, the front body panel 4 can be provided with a different shape than the rear body panel 6. For example, the undergarment can be configured as a thong shaped undergarment with a relatively narrow rear body panel 6. Various shapes and other acceptable wave patterns that can be used for the body panels are described for example in U.S. patent application Ser. No. 10/261,805, filed on Oct. 1, 2002, the entire disclosure of which is hereby incorporated herein by reference.

Figure 1A:
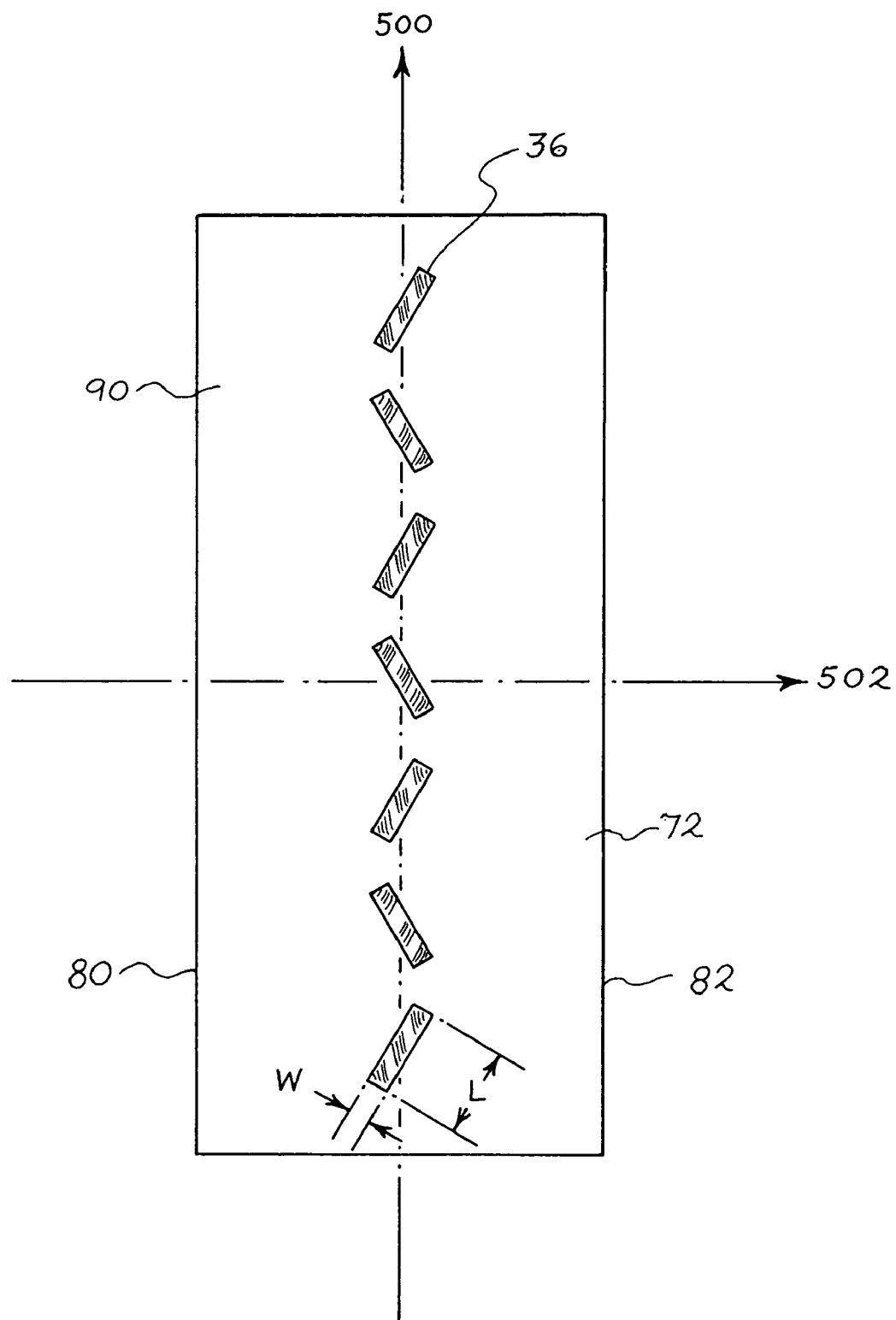
FIG. 1A is a plan view of a web of body material with a plurality of reinforcement elements being applied thereto.
Figure 1B:
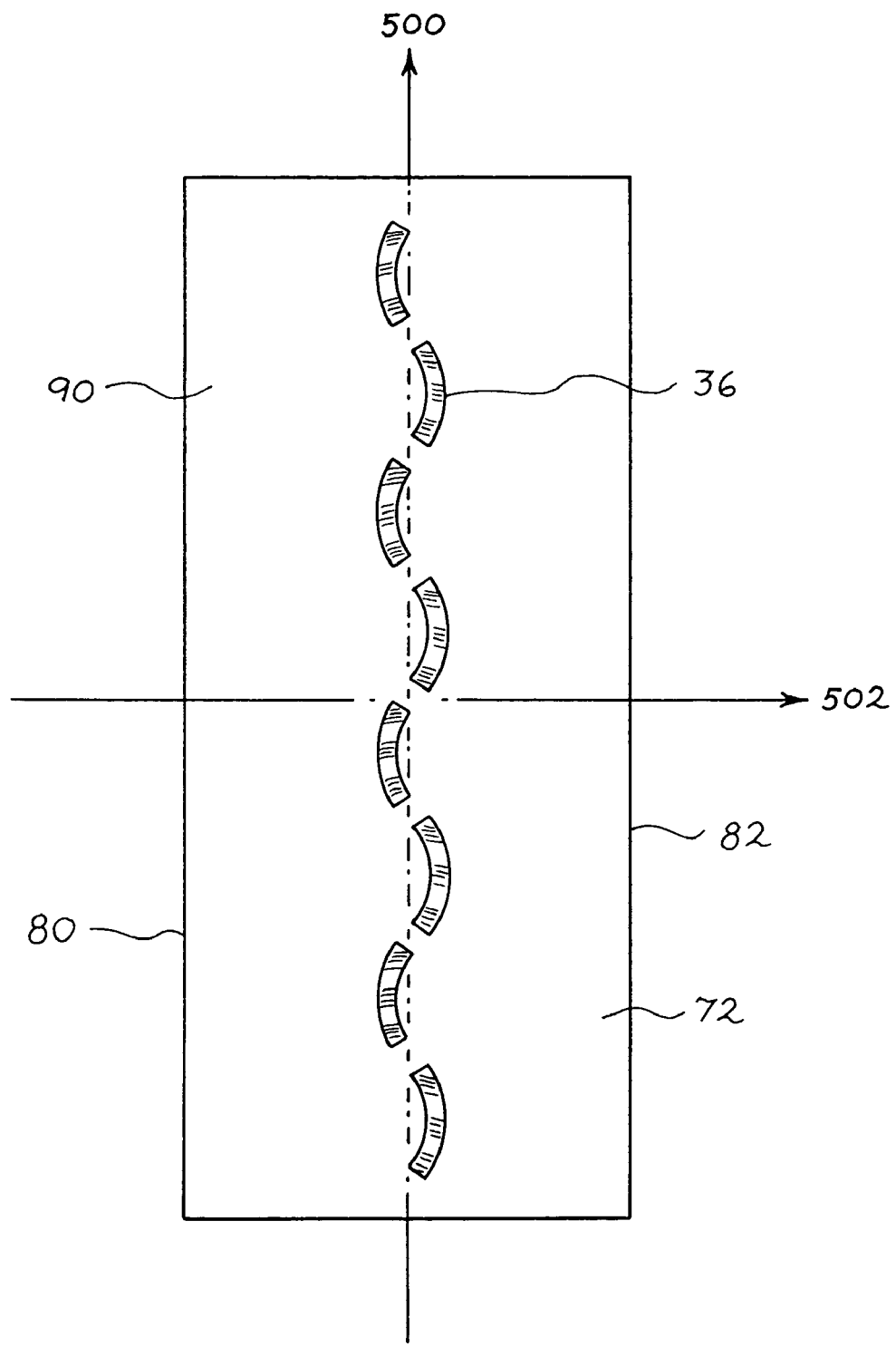
FIG. 1B is plan view of an alternative embodiment of a web of body material with a plurality of reinforcement elements being applied thereto.
Figure 2:
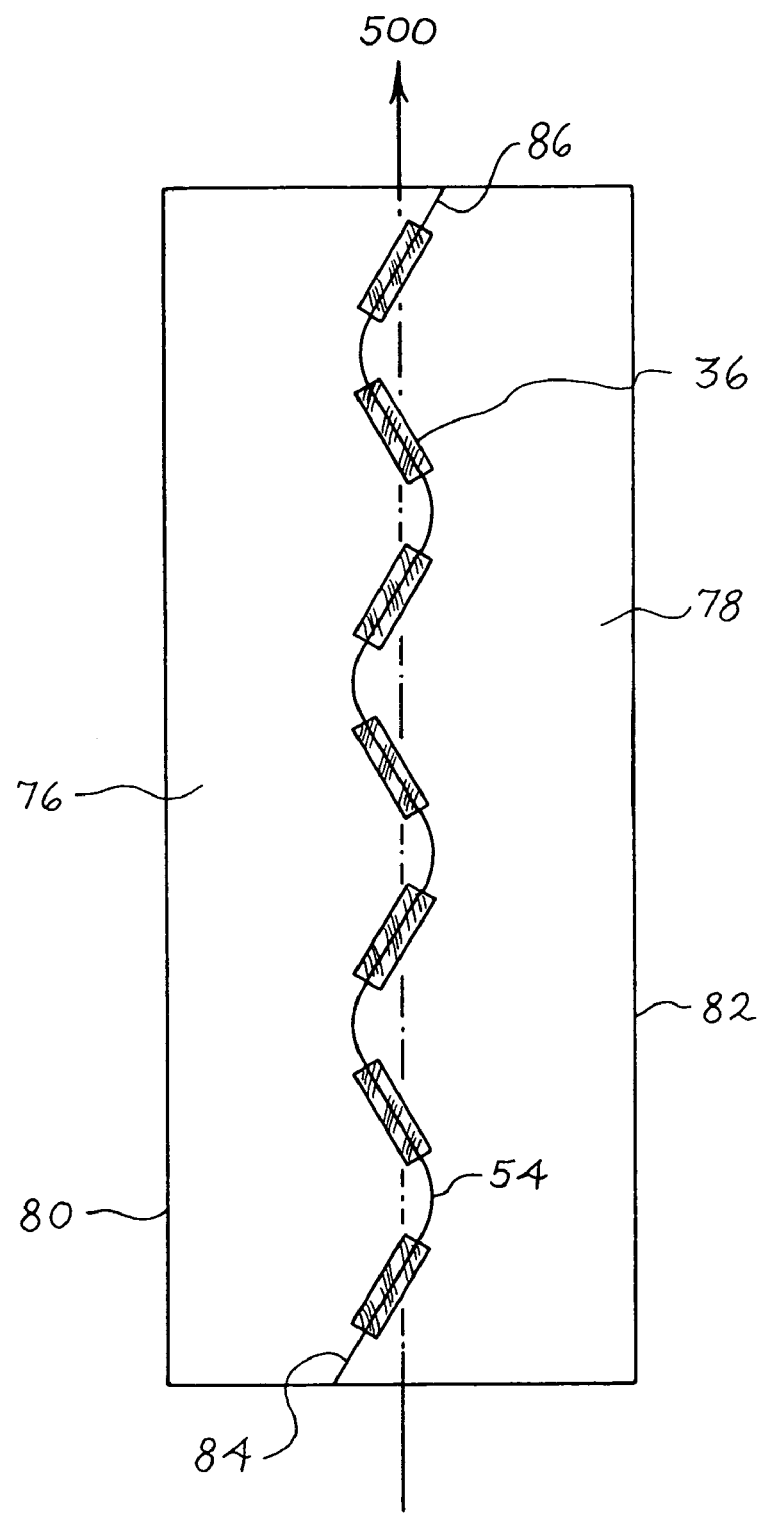
FIG. 2 is a plan view of a web of body panel material with a plurality of reinforcement elements being cut along a longitudinal machine direction.

Referring to FIGS. 1A, 1B and 7, one or both of the front and rear body panel webs are shifted in the longitudinal machine direction 500, so as to align the maximum rises or peaks and minimum rises or valleys. For example, as shown in FIG. 7, a first and second conveyor 102, 104 can be spaced apart so as to provide for a longer travel of one of the front and rear body panel webs.

Referring to FIGS. 1-3 and 7, the front and rear body panel webs 76, 78 are also separated, or shifted, outwardly relative to one another in the lateral cross-direction 502 so as to form a gap 88 between the cut edges 84, 86 of the front and rear body panel webs 76, 78 at the maximum rise formed at the respective peaks 54. In various embodiments, the spacing between the cut edges at the maximum rise of the respective front and rear body panels (i.e., the closest spacing between the front and rear body panels) is preferably between about 1% and about 90% of the total rise of the garment, more preferably between about 10% and about 60% of the total rise of the garment, and most preferably between about 20% and about 40% of the total rise of the garment. In an alternative embodiment, the cut edges and the crotch portions of the front and rear body panels overlap, and can be secured one to the other. In such an embodiment, the panels can be separated slightly, or can simply be shifted in the longitudinal direction without any lateral separation.

In one embodiment, the front and rear body panel webs 76, 78 are separated such that no portions of either web overlap each other. For example, as shown in FIG. 7, a first pair of rollers 106 can be angled or twisted to laterally spread the front and rear body panel webs 76, 78 a first amount before they are shifted in the longitudinal machine direction 500. A second pair of rollers 108 can be angled or twisted to laterally spread the front and rear body panel webs 76, 78 a second amount after they are shifted in the longitudinal machine direction 500. Of course, it should be understood that the front and rear body panels can be first shifted in the longitudinal machine direction 500 the desired amount and then separated in the lateral cross direction 502 the entire desired amount, or they can also be first separated in the lateral cross direction 502 the entire desired amount and then shifted in the longitudinal machine direction.

After the body panel webs 76, 78 are aligned and separated, regardless of the order thereof, a plurality of crotch members 50, for example absorbent inserts, are positioned in the lateral cross direction so as to bridge the gaps 88 between the body panel webs 76, 78 at successive peaks 54 where the maximum rises of the body panel webs are aligned. It should be understood that the term "gap" as used herein includes a "zero" distance between the respective cut edges, wherein the cut edges abut but do not overlap. The crotch members 50 are secured to the body panel webs 76, 78 as explained above. It should be understood that the crotch members 50 are preferably secured to a bodyside surface 90 of the body panel webs 76, 78, although they can also be secured to the garment side thereof. In a preferred embodiment, the crotch members, for example the absorbent inserts, are assembled offline and are then applied to the front and rear body panel webs 76, 78 as those webs are carried by a construction drum 110.

In one method, the crotch member is preferably rotated using an offset cam action rotator 112. The rotator includes a plurality of transfer segments 126, which can have a vacuum applied thereto, that engage the crotch member 50. Coupler arms 127 connect the transfer segments and drive a drive ring. The coupler arm 127 includes a cam end having a cam follower that follows the profile of a cam mechanism. The profile cam mechanism can be readily changed to change the desired speed output and pitch of the crotch member. The rotator 112 rotates the end portion of the transfer segment, preferably approximately 90 degrees, about a radial axis, such that the crotch member is oriented in the machine direction 500, as described above as the transfer segments are rotated about a horizontal axis 128. The rotator 112, and the method for the use thereof, is further disclosed in U.S. patent application Ser. No. 10/261,805, entitled "Three Piece Disposable Undergarment and Method for the Manufacture Thereof," filed Oct. 1, 2002 and U.S. patent application Ser. No. 10/325,500 entitled "Disposable Undergarment with a Stretchable Absorbent Insert and Method for the Use Thereof" filed Dec. 19, 2002, all of which are assigned to Kimberly-Clark Worldwide, Inc., the assignee of the present application, and the entire disclosures of all of which are hereby incorporated herein by reference.

After the crotch members 50 are secured to the body panel webs 76, 78 across the gap 88, the assembly is conveyed on a conveyor 114 to a helical folder 116, wherein the undergarments, and in particular the crotch members, are successively folded such that the front and rear body panel webs 76, 78 are positioned in an overlapping, or overlying relationship, preferably with the outer edges 80, 82 aligned. In various alternative embodiments, as shown in FIGS. 3 and 7, the body panel webs 76, 78 can be secured, for example by bonding, along a lateral cross direction at the area of minimum rise, or valleys 56 to form the side seam 48. The front and rear body panel webs 76, 78 are then cut along the lateral cross direction along the seam 48 to form a plurality of discrete disposable undergarments, each having a front and rear body panel 4, 6 and at least one reinforcement element 36 attached to the body side surface of the front and rear body panel 4,6.

Alternatively, the front and rear body panel webs 76, 78 can be first cut at the area of minimum rise, or valleys 56 and the crotch member 50 thereafter folded. In still another aspect, the front and rear body panel webs 76, 78 can be first cut thereby having at least a portion of the reinforcement element 36 on each of the front and rear body panel 4,6. Various refastenable fastening members can be applied to the front and rear body panels 4, 6 or front and rear body panel webs 76, 78 before or after the various cutting and folding operations. In yet another embodiment, as explained above, the undergarment can be configured with side seams which secure the front and rear body panels, and refastenable fastening members, which bridge lines of weakness formed in one or the other of the body panels.

In one embodiment, the reinforcement elements 36 are applied to an outer surface (body or garment side) of the web 72 of body panel material prior to cutting the web 72 to form the front and rear body panel webs 76, 78. The web is then cut to form the crotch edge, with the reinforcement elements being simultaneously cut. The reinforcement elements 36 can be applied to the web 72 such that approximately ½ of the reinforcement element 36 width (W) is positioned on each of the front and rear body panel webs 76, 78, or such that a greater portion of the width (e.g., between about 50% and about 90% is positioned on one of the front and rear body panel webs, with the remainder positioned on the other of the front and rear body panel webs. Of course, the entirety of the width of the reinforcement element can be positioned on either side of the cut defining the front and rear body panel webs. Moreover, it should be understood that a cut edge of the reinforcement element may be curvilinear as it follows the cut edge of the body panel. For example, the cut edge of the reinforcement element may have a convex and a concave portion as shown in FIG. 4.

In an alternative embodiment, the reinforcement elements 36 are secured to the web of body panel material such that they entirety of the width of the reinforcement element is disposed on only the front body panel web or only the rear body panel web after the web of body panel material is cut in the longitudinal machine direction. In another embodiment, the reinforcement elements 36 are secured to one or both of the front and rear body panel webs after they are formed by the die cutter, or other cutting operation. In any of these embodiments, the reinforcement elements 36 care applied to the web in a non-continuous and intermittently spaced configuration along the longitudinal direction such that they are incorporated along only the leg opening portions 18, 26 of the body panel webs and body panels after the web of body panel material is cut. Alternatively, the reinforcement elements 36 also can be applied, either continuously or non-continuously along the longitudinal direction adjacent the waist terminal edges 20, 28.

The reinforcement elements 36 are applied to the outer surface of the garment side or body side surface of the web 72 of body panel material. The reinforcement elements can be applied by bonding, including adhesive, ultrasonic and pressure bonding, and/or stitching, pinning and other known methods of attachment. Referring to FIG. 7, a roll of a web of reinforcement material 37 is rotated. The web of reinforcement material 37 is slip cut to form a plurality of discrete reinforcement elements 36, which are separated by an off set cam action roller 113. The off set cam action roller 113 desirably has at least an even number of transfer segments 129, for example six transfer segments, that engage of the reinforcement elements 36 and apply them to the web 72 of body panel material. It should be further understood that the application of the reinforcement elements can be performed before or after cutting the web 72 of body panel material. Furthermore, each reinforcement element 36 is applied to the web such that the axis of length is non-parallel to the axis of the longitudinal machine direction 500. In one embodiment, the reinforcement elements are alternatively and successively placed between about (+/−) 0 and 75 degrees from an axis defining the machine direction 500 and more desirably between about (+/−) 30 and 60 degrees from an axis 500. The reinforcement elements are successively positioned at positive and negative angles relative the axis 500 with reference to the leading edge of the reinforcement element. In one embodiment, the reinforcement elements can be spaced between about ½ P apart from each other, such that they are positioned at specific locations corresponding to the leg openings 18, 26. In one embodiment, the leading/tailing edges of the reinforcement elements 36 are applied adjacent to the seam 48 of both edges of the garment and may underlie portions of the seam.

The pitch (P) of the undergarment can be easily and quickly adjusted without the need to change over to new dies. The term "pitch" as used herein means the distance between any two adjacent things in series, and in particular between the valleys 56 or side edges 30, 32 of the finished undergarment. In particular, the web 72 of body panel material is simply stretched or elongated various predetermined amounts before it is cut to form the front and rear body panel webs 76, 78. For example, the largest waist/hip size is provided when the web 72 of body panel material is introduced into the cutting operation, or die cutter, with no elongation or stretch in the longitudinal machine direction. The smallest waist/hip size is provided when the web 72 of body panel material is elongated or stretched to its maximum capability, such that after the cutting operation, the front and rear body panel webs 76, 78 retract to form a garment having a smaller pitch (P) between the valleys. It should be understood that the reinforcement elements 36 can be elongated in conjunction with the web 72 of body panel material.

In one embodiment, the elongation of the body panel material is between about 20% and about 400%, in another embodiment the elongation is between about 50% and about 300%, and in another embodiment the elongation is between about 100% and about 200%. The final size or pitch of the undergarment is also determined by the process and positioning of the side seams, and the distance therebetween.

The rise (R) of the undergarment, measured between the outer edges 20, 28, also can be easily and quickly adjusted without the need to change over to new dies. In particular, the front and rear body panel webs 76, 78 are simply spaced apart in the lateral cross direction varying amounts, preferably with the gap being less than the length of the crotch member. For example, for a smaller garment having a lesser rise, the front and rear body panel webs 76, 78 are spaced closer together, with a smaller gap 88, than for a garment having a greater rise.

Preferably, the same crotch member 50 can be used in any of the garments, regardless of the pitch and rise. In this way, the overall simplicity and efficiency of the system and method is greatly improved, and there is no need to maintain inserts of different sizes in inventory, or to provide manufacturing capabilities to produce different size inserts. Indeed, one embodiment of the method provides for a system of manufacturing a three-piece disposable undergarment having reinforced leg and waist reinforcement elements with minimal waste, while providing flexibility to manufacture different size garments at minimal cost.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An absorbent garment comprising:
    a front body panel comprising a first pair of opposite side edges spaced equidistance from a longitudinally extending centerline, a first terminal waist edge, a first terminal crotch edge longitudinally spaced from said first terminal waist edge along at least said centerline, a first outermost body side surface and a first outermost garment side surface;
    a rear body panel comprising a second pair of opposite side edges, a second terminal waist edge, a second terminal crotch edge longitudinally spaced from said second terminal waist edge along at least said centerline, a second outermost body side surface and a second outermost garment side surface, wherein said second terminal crotch edge is longitudinally spaced from said first terminal crotch edge along at least said centerline so as to form a gap between said first and second terminal crotch edges, and wherein said first and second terminal crotch edges intersect said centerline;
    a crotch member connecting said front and rear body panels, said crotch member bridging said gap and extending across said first and second terminal crotch edges of said front and rear body panels along at least said centerline, wherein said crotch member is directly connected to each of said front and rear body panels; and
    at least one reinforcement element having a length and a width, said at least one reinforcement element secured directly to at least one of said first and second outermost body side surfaces and said first and second outermost garment side surfaces of said front and rear body panels adjacent to at least one of said first and second terminal crotch edges of said respective front and rear body panels.

2. The absorbent garment of claim 1 wherein said at least one reinforcement element comprises a stretchable material.

3. The absorbent garment of claim 1 wherein said at least one reinforcement element comprises at least one layer of non-woven material.

4. The absorbent garment of claim 1 wherein said at least one reinforcement element comprises at least one elastic strand.

5. The absorbent garment of claim 1 wherein said at least one reinforcement element comprises a least one strand of elastic laminate.

6. The absorbent garment of claim 1 wherein said at least one reinforcement element is disposed on said first outermost body side surface of said front body panel.

7. The absorbent garment of claim 1 wherein said at least one reinforcement element is disposed on said second outermost body side surface of said rear body panel.

8. The absorbent garment of claim 1 wherein said at least one reinforcement element is disposed on each of said first and second outermost body side surfaces of said front and rear body panels.

9. The absorbent garment of claim 1 wherein said at least one reinforcement element comprises a plurality of spaced apart reinforcement elements laterally spaced between at least one of said first and second pairs of opposite side edges.

10. The absorbent garment of claim 1 wherein said length of said at least one reinforcement element is between about 10% and about 50% of a lateral width of at least one of said front and rear body panels.

11. The absorbent garment of claim 10 wherein said length of said at least one reinforcement element is between about 20% and about 45% of said lateral width of at least one of said front and rear body panels.

12. The absorbent garment of claim 11 wherein said length of said at least one reinforcement element is between about 25% and about 40% of said lateral width of at least one of said front and rear body panels.

13. The absorbent garment of claim 1 wherein said at least one reinforcement element is bonded to said at least one of said first and second outermost body side surfaces and said first and second outermost garment side surfaces of said front and rear body panels.

14. The absorbent garment of claim 1 wherein said at least one reinforcement element comprises at least one first reinforcement element, and further comprising at least one second reinforcement element having a length and a width and secured to at least one of said first and second outermost body side surfaces and said first and second outermost garment side surfaces of said front and rear body panels adjacent to at least one of said first and second terminal waist edges of said respective front and rear body panels.

15. The absorbent garment of claim 1 wherein said crotch member comprises an absorbent insert.

16. The absorbent garment of claim 1 wherein at least one of said front and rear body panels are made of an elastic material.

17. The absorbent garment of claim 1 wherein said front body panel comprises a laminate structure having at least a first substrate defining said first outermost body side surface and a second substrate defining said first outermost garment side surface.

18. The absorbent garment of claim 17 further comprising at least one elastic strand disposed between said first and second substrates.

19. The absorbent garment of claim 17 further comprising a waist reinforcement element secured to one of said first outermost body side surface and said first outermost garment side surface of said front body panel along said first terminal waist edge.

20. The absorbent garment of claim 1 wherein said rear body panel comprises a laminate structure having at least a first substrate defining said second outermost body side surface and a second substrate defining said second outermost garment side surface.

21. The absorbent garment of claim 20 further comprising at least one elastic strand disposed between said first and second substrates.

22. The absorbent garment of claim 20 further comprising a waist reinforcement element secured to one of said second outermost body side surface and said second outermost garment side surface of said rear body panel along said second terminal waist edge.

23. An absorbent garment comprising:
   a front body panel comprising a first pair of opposite side edges, a first terminal waist edge, a first terminal crotch edge longitudinally spaced from said first terminal waist edge and extending laterally between said first pair of opposite side edges, a first outermost body side surface and a first outermost garment side surface;
   a rear body panel comprising a second pair of opposite side edges, a second terminal waist edge, a second terminal crotch edge longitudinally spaced from said second terminal waist edge and extending laterally between said second pair of opposite side edges, a second outermost body side surface and a second outermost garment side surface, wherein said second terminal crotch edge is longitudinally spaced from said first terminal crotch edge so as to form a gap between said first and second terminal crotch edges;
   a crotch member connecting said front and rear body panels, said crotch member bridging said gap and extending across said first and second terminal crotch edges of said front and rear body panels, wherein said crotch member is directly connected to each of said front and rear body panels; and
   a plurality of reinforcement elements each having opposite ends defining a length, said plurality of reinforcement elements positioned end to end along at least one of said first and second terminal crotch edges, wherein said plurality of reinforcement elements are secured directly to at least one of said first and second outermost body side surfaces and said first and second outermost garment side surfaces of said front and rear body panels.

24. The absorbent garment of claim 23 wherein at least a portion of said first and second terminal crotch edges are curved and wherein each of said plurality of reinforcement elements are linear.

25. The absorbent garment of claim 23 wherein adjacent ends of said plurality of reinforcement elements are laterally spaced apart.

26. The absorbent garment of claim 23 wherein each of said plurality of reinforcement elements comprises at least one layer of non-woven material.

* * * * *

UNITED STATES PATENT AND TRADEMARK OFFICE
CERTIFICATE OF CORRECTION

PATENT NO. : 7,621,900 B2 Page 1 of 1
APPLICATION NO. : 10/746212
DATED : November 24, 2009
INVENTOR(S) : Van Gompel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1391 days.

Signed and Sealed this

Twenty-sixth Day of October, 2010

David J. Kappos
*Director of the United States Patent and Trademark Office*